US005511542A

United States Patent [19]

Hall

[11] Patent Number: 5,511,542

[45] Date of Patent: Apr. 30, 1996

[54] LOX BREATHING SYSTEM WITH GAS PERMEABLE-LIQUID IMPERMEABLE HEAT EXCHANGE AND DELIVERY HOSE

[75] Inventor: Mark N. Hall, Richland, Wash.

[73] Assignee: Westinghouse Electric Corporation, Pittsburgh, Pa.

[21] Appl. No.: 220,865

[22] Filed: Mar. 31, 1994

[51] Int. Cl.$^6$ .............................. A62B 7/00; A61M 16/00

[52] U.S. Cl. ................................ 128/201.21; 128/201.29; 128/202.19; 128/204.15; 128/205.22; 62/259.3; 62/50.2

[58] Field of Search .......................... 128/204.21, 204.23, 128/201.21, 201.29, 202.11, 202.12, 205.20, 200.24, 201.13, 201.21, 201.29, 202.11, 204.18, 204.26, 205.22, 202.19, 204.15; 62/259.3, 50.2, 50.7

[56] References Cited

U.S. PATENT DOCUMENTS

| | | | |
|---|---|---|---|
| 3,049,896 | 8/1962 | Webb . | |
| 3,064,448 | 11/1962 | Whittington | 128/201.21 |
| 3,117,426 | 1/1964 | Fischer et al. . | |
| 3,161,192 | 12/1964 | McCormack | 128/201.21 |
| 3,227,208 | 6/1966 | Potter, Jr. et al. | 128/201.21 |
| 3,291,126 | 12/1966 | Messick . | |
| 3,345,641 | 10/1967 | Jennings . | |
| 3,457,918 | 7/1969 | Dibelius et al. | 128/201.29 |
| 3,648,289 | 3/1972 | Moreland . | |
| 3,714,942 | 2/1973 | Fischel et al. | 128/201.21 |
| 3,744,555 | 7/1973 | Fletcher et al. | 62/259.3 |
| 4,024,730 | 5/1977 | Bell et al. . | |
| 4,271,833 | 6/1981 | Moretti . | |
| 4,378,011 | 3/1983 | Warncke et al. . | |
| 4,403,608 | 9/1983 | Warncke . | |
| 4,691,760 | 9/1987 | Gupta et al. . | |
| 4,875,477 | 10/1989 | Waschke et al. . | |
| 4,881,539 | 11/1989 | Pasternack . | |
| 4,903,694 | 2/1990 | Hager . | |
| 5,027,807 | 7/1991 | Wise et al. . | |
| 5,186,869 | 2/1993 | Stumpf et al. . | |
| 5,197,294 | 3/1993 | Galvan et al. . | |
| 5,309,901 | 5/1994 | Beaussant | 128/201.29 |
| 5,358,689 | 10/1994 | Jonel et al. | 422/46 |
| 5,361,591 | 11/1994 | Caldwell | 62/50.4 |
| 5,365,745 | 11/1994 | Caldwell | 62/50.4 |

*Primary Examiner*—Edgar S. Burr
*Assistant Examiner*—Virendra Srivastava

[57] ABSTRACT

Life support apparatus composed of: a garment (2): for completely enclosing a wearer and constructed for preventing passage of gas from the environment surrounding the garment (2); a portable receptacle (6) holding a quantity of an oxygen-containing fluid in liquid state, the fluid being in a breathable gaseous; state when at standard temperature and pressure; a fluid flow member (16) secured within the garment (2) and coupled to the receptacle (6) for conducting the fluid in liquid state from the receptacle (6) to the interior of the garment (2); and a fluid flow control device (14) connected for causing fluid to flow from the receptacle (6) to the fluid flow member (16) at a rate determined by the breathable air requirement of the wearer, wherein fluid in liquid state is conducted into the interior of the garment (2) at a rate to be vaporized and heated to a breathable temperature by body heat produced by the wearer.

13 Claims, 2 Drawing Sheets

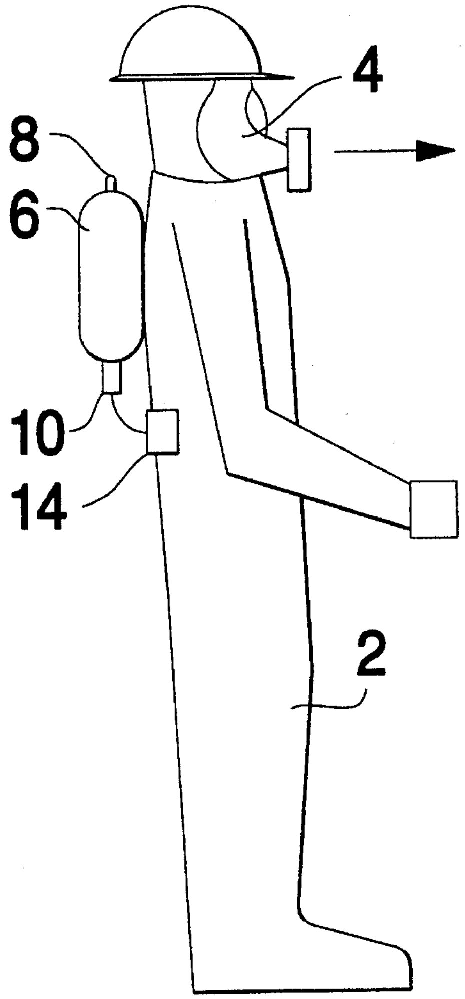
Figure 1
Figure 2
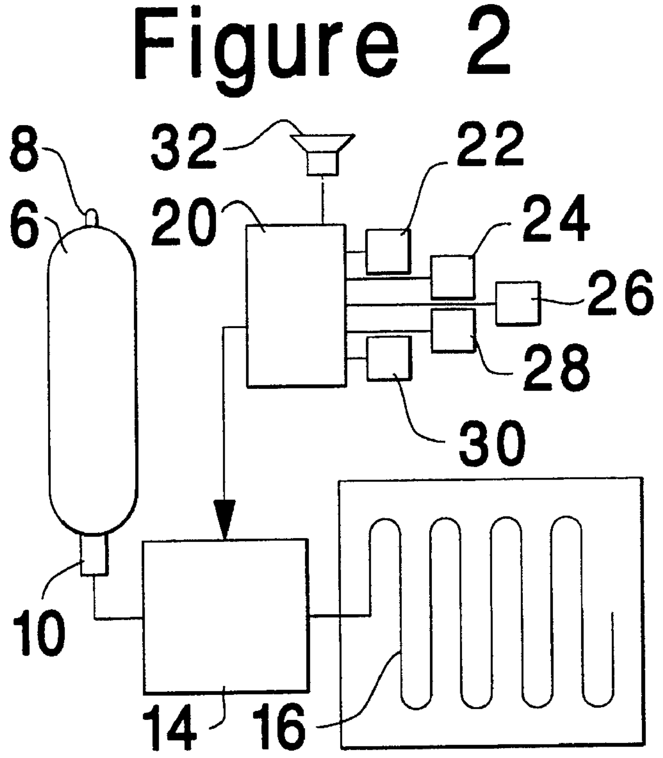
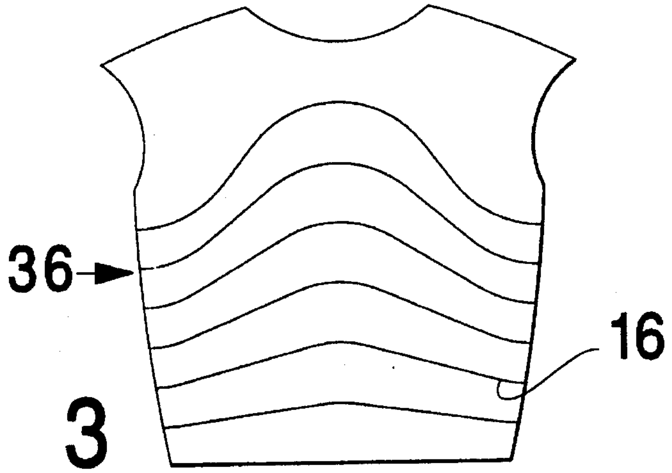
Figure 3

LOX BREATHING SYSTEM WITH GAS PERMEABLE-LIQUID IMPERMEABLE HEAT EXCHANGE AND DELIVERY HOSE

ORIGIN OF THE INVENTION

This invention was conceived or first reduced to practice in the course of, or under, Contract Number DE-ACO6-87RL10930 between the Westinghouse Hanford Company and the United States Government, represented by the Department of Energy. The United States Government may have rights in this invention.

BACKGROUND OF THE INVENTION

The present invention relates to a suit which will isolate a wearer from the environment, particularly to provide contamination protection, and which includes a combined supply of breathable air and a body air conditioning system.

Many occupations, including those existing in the nuclear industry, require that workers be outfitted in airtight suits which protect them from radioactive surface contamination and/or toxic gasses. Generally, these suits, by their nature, provide a high level of thermal insulation so that, particularly in a warm environment, the thermal gain within the suit is such as to cause the wearer to experience abnormal perspiration, resulting in considerable discomfort and rapid fatigue. Of course, this limits the length of time during which work can be performed while wearing such a suit, as well as the quality of that work. In an effort to obviate these difficulties, a variety of air conditioned suits have been proposed. Typically, such suits present substantial power requirements, in the range of 1–2 hp. Since such power requirements can not be satisfied, in practice, by batteries, these suits must be connected to heavy, non-portable power supplies. Liquid fuel powered air conditioners have also been proposed, but have been found unacceptable due to heat rejection problems as well as restrictions on bringing a combustible hydrocarbon fuel into certain work areas.

Compressed air umbilical-cord type air conditioned suits which utilize vortex cooling nozzles to expand air into the suit for cooling have also been proposed. Such suits are presently considered state-of-the-art for use in the nuclear industry, state and federal fire fighting organizations and the military for hazardous environments. These suits have a limited mobility and extremely limited range because they must be connected to a compressor support unit by an umbilical cord which must have a limited length in order to operate properly and avoid tangling of the cord.

In addition, for use in environments which do not have breathable air, workers must be provided with an air supply, use typically being made of scuba tanks, or bottles. These bottles are relatively heavy and bulky and can generally carry a maximum of a thirty minute air supply.

SUMMARY OF THE INVENTION

It is an object of the present invention to provide a protective suit which is free of the above-described shortcomings.

A more specific object of the invention is to provide a protective suit having a completely portable supply of breathing air and an essentially passive air conditioning system.

A further object of the invention is to provide a protective suit which carries an air supply and is light in weight.

Another object of the invention is to provide a protective suit having the capabilities described above and having an air supply which supplies a larger quantity of breathable air than prior self-contained air supplies.

The above and other objects are achieved, according to the present invention, by life support apparatus comprising: a garment for completely enclosing a wearer and constructed for preventing passage of gas from the environment surrounding the garment; a portable receptacle holding a quantity of an oxygen-containing fluid in liquid state, the fluid being in a breathable gaseous state when at standard temperature and pressure; fluid flow means secured within the garment and coupled to the receptacle for conducting the fluid in liquid state from the receptacle to the interior of the garment; and fluid flow control means connected for causing fluid to flow from the receptacle to the fluid flow means at a rate determined by the breathable air requirement of the wearer, wherein fluid in liquid state is conducted into the interior of the garment at a rate to be vaporized and heated to a breathable temperature by body heat produced by the wearer.

The invention is based to a substantial extent on recognition that the heat generated by the wearer as the effort exerted by the wearer varies corresponds to the heat necessary to vaporize liquid air initially at a temperature of about −320° F. to a breathable temperature and cause the vaporized air to maintain the interior of a garment at a suitable temperature.

A further novel feature of the invention resides in conducting liquid air through the garment via a conduit of a material which is permeable to water vapor and air in the gaseous state, but is impermeable to liquid oxygen or liquid air. This enables the liquid air to be humidified as it is being warmed and converted to the gaseous state.

BRIEF DESCRIPTION OF THE DRAWINGS

FIG. 1 is a pictorial view of a protective suit according to the invention.

FIG. 2 is a schematic diagram of a breathing air supply and air conditioning system according to the invention.

FIG. 3 is a simplified elevational view of a vest forming part of the suit according to the invention.

DESCRIPTION OF THE PREFERRED EMBODIMENTS

Figures 4, 5, 6:
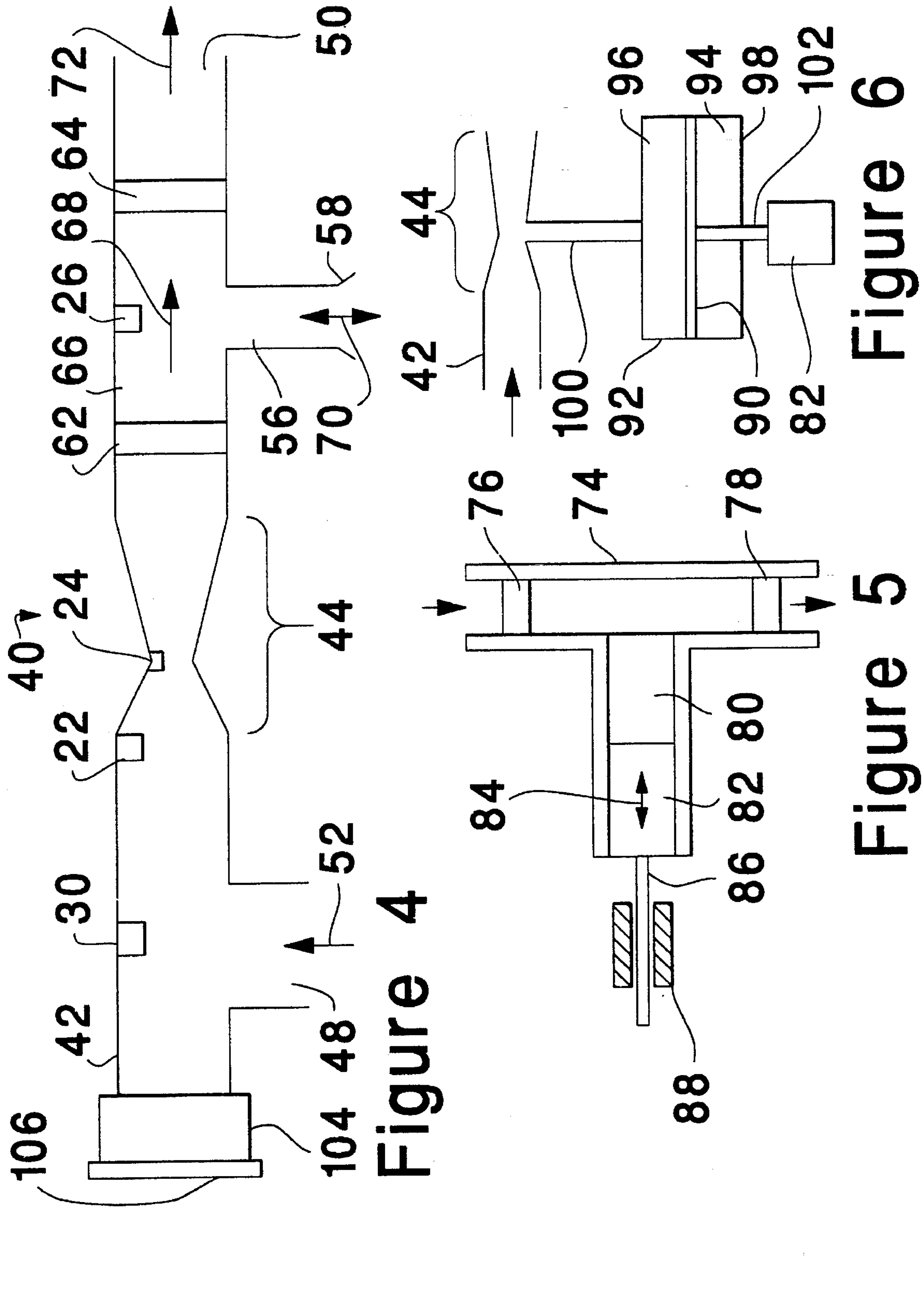
FIG. 4 is a simplified pictorial view of an example of an air delivery system of a protective suit according to the invention.
FIG. 5 is a simplified cross-sectional view of a liquid air control unit of a protective suit according to the invention.
FIG. 6 is a simplified cross-sectional view of an alternative arrangement for controlling liquid air flow in a protective suite according to the invention.

FIG. 1 is a simplified pictorial view showing a life support device according to the invention. This device includes a garment 2 which is to be worn in a manner to completely enclose the wearer. Garment 2 includes a face mask 4 provided, in a conventional manner, with viewing windows and a device including a one-way valve via which exhalate will be expelled from the interior of the garment. Garment 2 is made of a material which prevents passage of air at least from the environment surrounding garment 2. Preferably, garment 2 is completely impermeable to the passage of gas in either direction, other than the passage of exhalate from the wearer. Garment 2 carries a receptacle 6 which is preferably cryoinsulated and constitutes a reservoir for liquified air, which has been brought to a temperature equal to or below −325° F.

Receptacle 6 is equipped with a pressure relief valve 8 which permits air to be expelled, as needed, in order to maintain the pressure within receptacle 6 at a pressure slightly above atmospheric, e.g. a pressure of 1.25 atmospheres absolute.

Receptacle 6 further includes a liquified air outlet coupling 10 via which liquified air is supplied to an inlet of a metering valve 14. Metering valve 14 is also carried by garment 2.

Metering valve 14 has a fluid outlet connected to a conduit 16 which is secured to the interior surface of garment 2 and forms a heat exchanger via which body heat developed by the wearer is absorbed by liquified air to cause the liquified air to enter its gaseous state.

Conduit 16 may have an outlet end coupled to breathing mask which covers the wearer's nose and/or mouth inside of face mask 4. However, according to preferred embodiment of the invention, such a breathing mask need not be provided and conduit 16 is made of a material which is impermeable to liquids but permeable to gasses.

By way of non-limiting example, a conduit 16 having this capability may be composed of a Dacron (TM) tube having a diameter of 0.25" and a wall thickness of 0,006" and a sheath of nonwoven cotton having a layer thickness of 0.375", surrounding and in contact with the tube.

When the conduit has the preferred form according to the invention, moist air trapped in garment 2, the moisture resulting primarily from evaporated perspiration, will be absorbed in the liquid air to give the liquid air a certain moisture content. As liquid air evaporates, it can pass through the wall of conduit 16 to the region enclosed by garment 2. There, the gaseous, breathable air can further absorb moisture present within the region enclosed by garment 2. Thus, whereas vaporized liquid air would normally have essentially zero water content, liquid air which has undergone a phase change to the gaseous state a device according to the present invention can be made to have a relative humidity which the wearer will find to be comfortable.

In addition, moisture transferred from the interior of garment 2 to liquid within conduit 16 produces additional heat transfer to the liquid in addition to increasing the moisture content of the fluid which is subsequently evaporated.

Conduit 16 may be fitted into a vest worn inside of garment 2. Such vest would surround the wearer's torso and conduit 16 may be configured to follow a serpentine or helical path over the interior surface of the vest. Alternatively, conduit 16 may be installed in garment 2 in a manner to extend around the torso and one or more limbs of the wearer.

According to the invention, conduit 16 is arranged so that, in conjunction with the thermal insulation provided by garment 2, a very high percentage of the body heat generated by the wearer is absorbed by the liquid flowing through conduit 16. If a sufficiently high percentage of this heat is thus absorbed, the rate at which heat is absorbed will closely approximate the rate at which heat must be supplied to liquid air which initially has a temperature of −325° F. to evaporate the amount of air required by the wearer and to heat that air to a temperature of the order of 80° F. By way of example, a 154 lb. adult male will, when moderately active, i.e. walking and performing moderate lifting or pushing, consume about 100 cubic feet of breathable air and generate about 1000–1400 BTU/hour of heat. The heat needed to cause liquid air at −320° F. to be evaporated and heated to a temperature of 80° F. is of the order of 1350 BTUs per 100 cubic feet breathable air. In addition, such a wearer will produce between 1 and 1.5 lbs. of perspiration, the evaporation enthalpy of water being of the order of 1045 BTU/lb. The moisture requirements for humidifying breathable air is only about 0,084 lb/gallon of liquid air. Excess perspiration moisture can be absorbed by garment 2 and any clothing worn by the wearer underneath garment 2, and this moisture can pass, by capillary action, through garment 2 and evaporate to the surrounding environment.

In further accordance with the invention, the rate of delivery of liquid air, via metering valve 14, is controlled on the basis of monitored parameters representative of the wearer's breathing requirement. Specifically, as shown in FIG. 2, metering valve 14 is controlled by a control device 20 connected to receive signals from one or more sensors. The sensors may include pressure sensors 22 and 24, an acoustic signal sensor 26, typically a microphone, a temperature sensor 28 and an oxygen sensor 30. As will be explained in greater detail below, pressure sensors 22 and 24 are disposed to provide an indication of the rate of delivery of breathable air to the wearer. Control device 20 is further connected to an alarm device 32, for producing an audible alarm for example, installed in garment 2.

Control device 20 may include a microprocessor which derives, from the signals provided by sensors 22 and 24, a signal for controlling metering valve 14. By way of example, the signal provided by control device 20 may be in the form of a train of pulses having a repetition rate corresponding to the rate at which liquid air should be delivered to conduit 16 in order to supply breathable air at the rate required by the wearer. In this case, metering valve 14 would be of a type which delivers a measured quantity of liquid air to conduit 16 in response to each control signal pulse.

Control device 20 may also be connected to a pressure sensor which is disposed to sense the wearer's breathing rate, which is directly linked to the rate at which liquid air must be supplied to the interior of garment 2.

According to an alternative embodiment of the invention, liquid air can be injected directly into the suit at a plurality of points. After injection, the liquid air would undergo phase change, expansion and moisture absorption without requiring the need for special conduits. Preferably, the liquid air would be injected via openings located in the upper half of garment 2, producing cool air which descends through the region enclosed by garment 2, while warm air rises to the top, where it is consumed by the wearer. Natural convection would then keep the interior of the garment at an approximately uniform temperature without requiring any forced air system.

In addition, a wearer may wear a surgical type mask, or other filter, to avoid inhaling bacteria present within garment 2.

According to a further embodiment of the invention, metering valve 14 may be in the form of an electric stepper motor and a positive displacement liquid pump to meter liquid air into garment 2. The wearer may have a breathing mouthpiece provided with a pressure transducer which measures both the breathing rate and depth and which supplies a signal to microprocessor in control unit 20 to compute the rate at which liquid air is to be conveyed from receptacle 6.

The microprocessor will provide signal to activate the pump and positively displace a the required amount of liquid air to the interior of garment 2.

In addition, garment 2 may be equipped with a digital readout device providing vital information such as the temperature within garment 2 and the quantity of liquid air remaining in receptacle 6.

FIG. 3 is a front view showing a vest 36 which may be worn underneath garment 2. Vest 36 carries conduit 16 which, in the illustrated embodiment, follows a generally spiral path around vest 36. Thus, in FIG. 3, the portions of conduit 16 which extend across the back of vest 36 are seen.

FIG. 4 illustrates, by way of example, a unit 40 which may be installed in garment 2 for directing, and controlling the delivery of air, to the wearer. Unit 40 is composed of a conduit, or pipe, 42 having a portion 44 which contains a constriction so that portion 44 defines a Venturi.

Pipe 42 has an air inlet 48 in communication with the interior of garment 2 and an air outlet 50 communicating witch the atmosphere surrounding garment 2. Air which has been heated to the gaseous state within garment 2 can flow through air inlet 48 in the direction of arrow 52. Pipe 42 is further provided with an air flow 56 which is connected with a breathing tube or mask 58. Breathing tube or mask 58 may be disposed within, or integral with, face mask 4 and may be constructed to establish air flow communication between passage 56 and the mouth and/or nose of the wearer in any manner known in the breathing apparatus art.

Within pipe 42 there are provided two pressure responsive one-way valves 62 and 64 delimiting and bounding a pipe region 66 which communicates with tube or mask 58. Each of valves 62 and 64 is oriented to permit air flow only in the direction of arrow 68.

Air flow through pipe 42 is controlled essentially by the wearer's breathing action. When the wearer inhales, a pressure differential will be created between inlet 48 and region 66 to cause valve 62 to open and allow air to flow through valve 62 and into tube or mask 58, as indicated by arrow 70. When the wearer exhales, the pressure in region 66 will rise to a sufficient extent to close valve 62 and open valve 64. Air then flows from tube or mask 58 to region 66, also indicated by arrow 70. When valve 64 is open, exhaled air will be exhausted in the direction of arrow 72 to the external atmosphere via valve 64 and air outlet 50. Under normal operating conditions, valve 62 is open only when the wearer is inhaling and valve 64 is open only when the wearer is exhaling so that air laden with carbon dioxide will be expelled to the atmosphere surrounding suit 2.

Pressure sensors 22 and 24 are disposed to sense the pressure at the inlet and point of constriction, respectively, of Venturi 44. Sensed pressure signals produced by sensors 22 and 24 are supplied to control device 20, where they are employed in a known manner to produce an indication of the mass rate of air flow through pipe 42.

Microphone 26 is disposed to receive breathing sounds and produces a signal which can be analyzed in control device 20 to identify the wearer's breathing rate and the depth, or volume, of each breath.

Control device 20 processes information from the signals supplied by sensors 22 and 24 and microphone 26 to determine the rate at which liquid air must be conveyed from receptacle 6 to meet the wearer's oxygen demand. This determination is used to produce an output signal in the form of a pulse train in which the product of energy content per pulse (pulse power level times pulse duration) and pulse repetition rate corresponds to the determined liquid air flow rate.

FIG. 5 shows one example of a metering valve which can control delivery of liquid air from receptacle 6. This valve includes a conduit 74 connected between coupling 10 and conduit 16, as shown in FIG. 2. Conduit 74 contains two one-way valves 76 and 78 installed to permit liquid air to flow only in the direction from coupling 10 to conduit 16. The region of conduit 74 between valves 76 and 78 is in communication with a cylinder 80 containing a piston 82. Piston 82 is movable in cylinder 80 in the direction of arrow 84 and is connected to a rod 86 that is coupled electromagnetically to a solenoid coil 88. Solenoid coil 88 is connected to receive the output signal from control device 20 so as to displace piston 82 from a normal, or starting, position in a direction indicated by arrow 84, in response to each pulse of the signal from control device 20. Piston 82 is biassed to the starting position when the signal provided by control device has a magnitude of zero, i.e. during periods between signal pulses. Piston 82 is displaced by each signal pulse by a distance corresponding to the pulse energy content.

Thus, during each pulse period, piston 82 will be. displaced in directions to alternatingly increase and decrease the volume of cylinder 80. Each time the volume of cylinder 80 is increased, liquid air is drawn from receptacle 6 and via valve 76, into the region between valves 76 and 78, including into cylinder 80. Each time the volume of cylinder 80 is decreased, liquid air is forced from the region between valves 76 and 78 and via valve 78 into conduit: 16.

As a result of the relation between the movements of piston 82 and the signal from control device 20, the above-described metering valve delivers liquid air to conduit 16 at a rate corresponding to the wearer's actual breathing demand.

An alternative, and simple, arrangement for controlling delivery of liquid air from receptacle 6 is shown in FIG. 6. This embodiment uses the pipe 42 of FIG. 4, possibly without sensors 22 and 24 and microphone 26, and uses the metering valve 74–82 of FIG. 5. In the embodiment of FIG. 6, a pressure responsive diaphragm 90 is disposed in a housing 92 in a manner to divide the interior of housing 92 into two chamber 94 and 96. Chamber 94 communicates with the environment around suit 2 via an orifice 98 and chamber 96 communicates with a point within Venturi 44 downstream of its constriction via a tube 100. Diaphragm 90 is mechanically connected to piston 82 by a rod 102.

The pressure at the constriction of Venturi 44 is proportional to the rate of flow of air in the gaseous state through pipe 42. The air flow rate through pipe 42 has a pulsating pattern controlled by the wearer's breathing pattern. Thus, the rate and magnitude of pressure pulsations transmitted to chamber 96 via tube 100 is representative of breathing demand. These pressure pulsations then displace diaphragm 90 in a manner to drive piston 82 to supply liquid air at the rate required to supply the actual breathing demand.

Reverting to FIG. 2, temperature sensor 28 is disposed in receptacle 6, preferably in a lower portion thereof, to provide a signal indicating the temperature within receptacle 6. When a liquid air container is almost empty, the temperature within the container rises.

Oxygen sensor 30 is disposed to monitor the oxygen content of air entering pipe 42 of FIG. 4. If the oxygen content is too high, this signifies that the nitrogen content of the air is too low, which is an undesirable condition.

The signals from sensor 28 and 30 are supplied to control device 20 and if either signal indicates a dangerous condition, control device 20 will activate alarm 32 in order to alert the wearer.

Reverting to FIG. 4, unit 40 further includes, at the inlet end of pipe 42, a filter 104 located at the outer surface of garment 2. Filter 104 is normally blocked, to prevent air flow therethrough, by a tear-off sheet 106. If alarm 32 is activated, or the wearer otherwise has difficulty breathing and can not reach an area where garment 2 can be safely removed, he may tear sheet 106 away from filter 104 to gain access to environmental air.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. Life support apparatus comprising:

a garment for completely enclosing a wearer and constructed for preventing passage of gas from the environment surrounding said garment;

a portable receptacle holding a quantity of an oxygen-containing fluid in liquid state, the fluid being in a breathable gaseous state when at standard temperature and pressure;

fluid flow means secured within said garment and coupled to said receptacle for conducting the fluid in liquid state from said receptacle to the interior of said garment; and flow control means connected for causing fluid to flow from said receptacle to said fluid flow means at a rate determined by the breathable air requirement of the wearer, wherein fluid in liquid state is conducted into the interior of the garment at a rate to be vaporized and heated to a breathable temperature by body heat produced by the wearer, and wherein said fluid flow means comprise a heat exchanger including a conduit connected to receive the fluid from said receptacle, said conduit being made of a material which is permeable to gasses and impermeable to liquids.

2. Apparatus as defined in claim 1 wherein said flow control means comprise controllable fluid metering means connected between said receptacle and at least a portion of said fluid flow means for controlling flow of fluid from said receptacle to said fluid flow means, and sensing means disposed for sensing a physical quantity representative of the wearer's breathable air requirement, said sensing means being connected to said fluid metering means for causing said fluid metering means to cause the fluid to flow from said receptacle at a rate proportional to the sensed physical quantity.

3. Apparatus as defined in claim 2 wherein the physical quantity is at least one of: the wearer's breathing rate; the humidity level within said garment; the air temperature within said garment; and the air pressure within said garment.

4. Apparatus as defined in claim 1 wherein said oxygen-containing fluid is air.

5. Apparatus as defined in claim 1 wherein said conduit is in contact with air inside said garment and follows a path which traverses a portion of said garment that is adjacent the wearer's chest when said garment is being worn.

6. Apparatus as defined in claim 5 wherein said conduit has a closed end and a length sufficient to assure that substantially all of the fluid received from said receptacle is evaporated by heat from the wearer's body before reaching said closed end.

7. Apparatus as defined in claim 6 wherein said flow control means comprise controllable fluid metering means connected between said receptacle and at least a portion of said fluid flow means for controlling flow of fluid from said receptacle to said fluid flow means, and sensing means disposed for sensing a physical quantity representative of the wearer's breathable air requirement, said sensing means being connected to said fluid metering means for causing said fluid metering means to cause the fluid to flow from said receptacle at a rate proportional to the sensed physical quantity.

8. Apparatus as defined in claim 7 wherein the physical quantity is at least one of: the wearer's breathing rate; the humidity level within said garment; the air temperature within said garment; and the air pressure within said garment.

9. Apparatus as defined in claim 8 wherein said oxygen-containing fluid is air.

10. Apparatus as defined in claim 9 further comprising a vest to be worn by the wearer under said garment and wherein at least a portion of said conduit is secured to said vest.

11. Apparatus as defined in claim 10 further comprising means for securing said receptacle to the wearer's body outside of said garment.

12. Apparatus as defined in claim 1 wherein said receptacle comprises a relief valve for maintaining a selected pressure above atmospheric within said receptacle.

13. Apparatus as defined in claim 1 further comprising means for securing said receptacle to the wearer's body outside of said garment.

* * * * *